US009994593B2

United States Patent
Yoshino et al.

(10) Patent No.: US 9,994,593 B2
(45) Date of Patent: Jun. 12, 2018

(54) COPPER COMPOUND, STARTING MATERIAL FOR FORMING THIN FILM, AND METHOD FOR MANUFACTURING THIN FILM

(71) Applicant: ADEKA CORPORATION, Tokyo (JP)

(72) Inventors: Tomoharu Yoshino, Tokyo (JP); Masaki Enzu, Tokyo (JP); Atsushi Sakurai, Tokyo (JP); Akihiro Nishida, Tokyo (JP); Makoto Okabe, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days. days.

(21) Appl. No.: 15/306,812

(22) PCT Filed: Apr. 8, 2015

(86) PCT No.: PCT/JP2015/060997
§ 371 (c)(1),
(2) Date: Oct. 26, 2016

(87) PCT Pub. No.: WO2015/174173
PCT Pub. Date: Nov. 19, 2015

(65) Prior Publication Data
US 2017/0044188 A1 Feb. 16, 2017

(30) Foreign Application Priority Data
May 14, 2014 (JP) ................... 2014-100611

(51) Int. Cl.
*C07F 1/08* (2006.01)
*C07C 215/08* (2006.01)
(Continued)

(52) U.S. Cl.
CPC .............. *C07F 1/08* (2013.01); *C07C 215/08* (2013.01); *C09D 1/00* (2013.01); *C09D 5/24* (2013.01);
(Continued)

(58) Field of Classification Search
None
See application file for complete search history.

(56) References Cited

U.S. PATENT DOCUMENTS

2012/0070981 A1 3/2012 Clendenning et al.
2013/0330473 A1* 12/2013 Winter ................... C23C 16/18
427/252

OTHER PUBLICATIONS

Extended European Search Report dated Dec. 1, 2017 in corresponding European Application No. 15793276.5.
(Continued)

*Primary Examiner* — Clinton A Brooks
(74) *Attorney, Agent, or Firm* — Wenderoth, Lind & Ponack, L.L.P.

(57) ABSTRACT

This invention provides a copper compound represented by General Formula (I) below. In General Formula (I), $R^1$ to $R^3$ independently represent a linear or branched alkyl group with a carbon number of 1 to 5; provided that $R^1$ and $R^2$ are a methyl group, $R^3$ represents a linear or branched alkyl group with a carbon number of 2 to 5; and provided that $R^1$ is a methyl group and $R^2$ is an ethyl group, $R^3$ represents a methyl group or a linear or branched alkyl group with a carbon number of 3 to 5. A starting material for forming a thin film of the present invention includes the copper compound represented by General Formula (I). The present invention can provide a copper compound which has a low melting point, can be conveyed in a liquid state, has a high vapor pressure, and is easily vaporizable, and also a starting material for forming a thin film which uses such a copper compound.

(Continued)

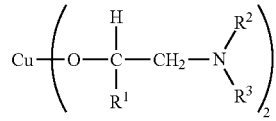

(I)

3 Claims, 1 Drawing Sheet

(51) Int. Cl.

| | | |
|---|---|---|
| *C23C 16/18* | (2006.01) | |
| *H01L 21/28* | (2006.01) | |
| *H01L 21/285* | (2006.01) | |
| *C09D 1/00* | (2006.01) | |
| *C09D 5/24* | (2006.01) | |
| *C23C 16/06* | (2006.01) | |
| *C23C 16/455* | (2006.01) | |

(52) U.S. Cl.
CPC .............. *C23C 16/06* (2013.01); *C23C 16/18* (2013.01); *C23C 16/45525* (2013.01); *C23C 16/45542* (2013.01); *H01L 21/28* (2013.01); *H01L 21/285* (2013.01)

(56) References Cited

OTHER PUBLICATIONS

Dey et al., "Mechanism for the Atomic Layer Deposition of Copper Using Diethylzinc as the Reducing Agent: A Density Functional Theory Study Using Gas-Phase Molecules as a Model", The Journal of Physical Chemistry, 116(35):8893-8901 (2012).

Muller et al., "Gas-phase loading of [Zn$_4$O(btb)$_2$] (MOF-177) with organometallic CVD-precursors: inclusion compounds of the type [L$_n$M]$_a$@MOF-177 and the formation of Cu and Pd nanoparticles inside MOF-177", Journal of Materials Chemistry, 18(43):5274-5281 (2008).

\* cited by examiner

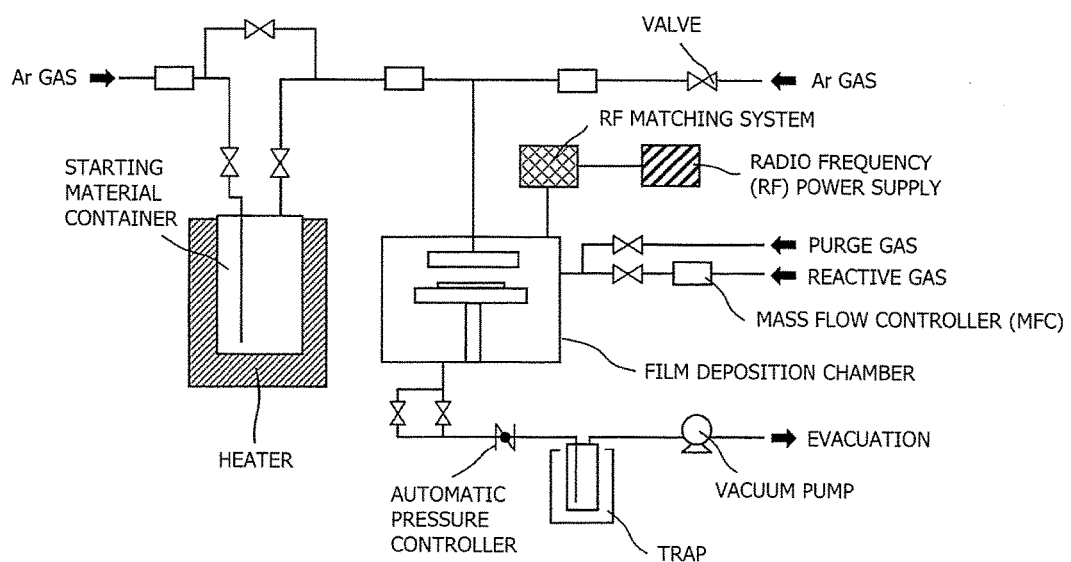

COPPER COMPOUND, STARTING MATERIAL FOR FORMING THIN FILM, AND METHOD FOR MANUFACTURING THIN FILM

TECHNICAL FIELD

The present invention relates to a copper compound, a starting material for forming a thin film, and a method for manufacturing a thin film that can be used for wiring materials for LSI, electrode materials, and the like.

BACKGROUND ART

Copper thin films and copper-containing thin films have been used for wiring materials for LSI (Large Scale Integration) and electrode materials because such films exhibit high electric conductivity, high resistance to electromigration, a high melting point, and the like. To manufacture such thin films, flame hydrolysis deposition methods, sputtering methods, ion plating methods, MOD (Metal Organic Decomposition) methods such as coating thermal decomposition methods and sol-gel methods, ALD (Atomic Layer Decomposition) methods, and vapor thin-film formation methods such as CVD (Chemical Vapor Decomposition) methods are used. Among them, the vapor thin-film formation methods are optimum manufacturing processes because they have a large number of merits. Thus, for example, they are suitable for mass production, excel in composition controllability and step coverage ability, and enable hybrid accumulation.

Copper compounds having an organic ligand have been used as a precursor for feeding copper atoms to the thin film in the MOD method or vapor thin-film formation method, the precursor being included in a starting material for forming the thin film.

For example, Patent Documents 1 and 2 report copper compounds including a tertiary amino alkoxide as a ligand. Further, Non Patent Document 1 reports a copper compound including a secondary amino alkoxide as a ligand.

REFERENCES

Patent Documents

Patent Document 1: KR 10-0675983 B
Patent Document 2: US 2010/0181566 A

Non Patent Document

Non Patent Document 1: Ralf Becker et al. "A Study on the Metal-Organic CVD of Pure Copper Films From Low Cost Copper (II) Dialkylamino-2-propoxides: Tuning of the Thermal Properties of the Precursor by Small Variations of the Ligand", Chemical Vapor Deposition, 2003, vol. 9, No. 3, pp. 149-156

DISCLOSURE OF THE INVENTION

Problems to be Solved by the Invention

In various methods for manufacturing a thin film, in particular, in the vapor thin-film formation method, the precursor used for the starting material for forming a thin film is required to have a low melting point, to be conveyable in a liquid state, to have a high vapor pressure, and to be easily vaporizable. However, the copper compounds of Patent Documents 1 and 2 and Non Patent Document 1 do not fully satisfy these requirements.

The present invention has been created to resolve the abovementioned problems, and it is an objective of the present invention to provide a copper compound that has a low melting point, can be conveyed in a liquid state, has a high vapor pressure, and is easily vaporizable, and also to provide a starting material for forming a thin film which uses such a copper compound.

It is another objective of the present invention to provide a method for manufacturing a thin film that is suitable for manufacturing a copper-containing thin film of good quality with good productivity.

Means for Solving the Problems

The results of the research conducted by the inventors have demonstrated that the abovementioned problems can be solved by a copper compound having an aminoalcohol of a specific structure as a ligand. This finding led to the creation of the present invention.

Thus, the present invention provides a copper compound represented by General Formula (I) below:

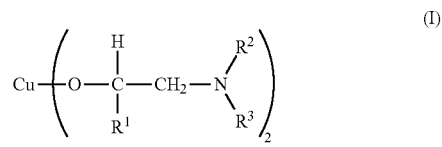

wherein, $R^1$ to $R^3$ independently represent a linear or branched alkyl group with a carbon number of 1 to 5; provided that $R^1$ and $R^2$ are a methyl group, $R^3$ represents a linear or branched alkyl group with a carbon number of 2 to 5; and provided that $R^1$ is a methyl group and $R^2$ is an ethyl group, $R^3$ represents a methyl group or a linear or branched alkyl group with a carbon number of 3 to 5.

The present invention also provides a starting material for forming a thin film which includes the copper compound.

The present invention also provides a method for manufacturing a thin film, comprising the steps of: vaporizing the starting material for forming a thin film to obtain a vapor including a copper compound; and contacting the vapor with a substrate to decompose and/or chemically react the copper compound and then form a thin film on the substrate.

Effects of the Invention

In accordance with the present invention, it is possible to provide a copper compound that has a low melting point, can be conveyed in a liquid state, has a high vapor pressure, and is easily vaporizable, and also to provide a starting material for forming a thin film which uses such copper compound.

In accordance with the present invention, it is also possible to provide a method for manufacturing a thin film that is suitable for manufacturing a copper-containing thin film of good quality with good productivity.

BRIEF DESCRIPTION OF THE DRAWINGS

FIG. 1 is a conceptual diagram of a plasma ALD device for use in the method for manufacturing a thin film in accordance with the present invention; this device was used in Example 8.

BEST MODE FOR CARRYING OUT THE INVENTION

The preferred embodiments of the copper compound, the starting material for forming a thin film, and the method for manufacturing a thin film in accordance with the present invention will be explained hereinbelow in greater detail.

The copper compound of the present invention is represented by General Formula (I) below.

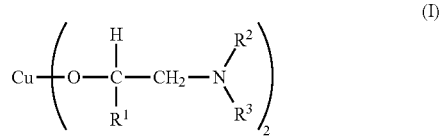

(I)

In General Formula (I), $R^1$ to $R^3$ independently represent a linear or branched alkyl group with a carbon number of 1 to 5. The linear or branched alkyl group with a carbon number of 1 to 5 which is represented by $R^1$ to $R^3$ is not particularly limited, and examples thereof include a methyl group, an ethyl group, a propyl group, an isopropyl group, a butyl group, an isobutyl group, a sec-butyl group, a tert-butyl group, a pentyl group, an amyl group, and an isoamyl group. However, when $R^1$ and $R^2$ are a methyl group, $R^3$ represents a linear or branched alkyl group with a carbon number of 2 to 5; and when $R^1$ is a methyl group and $R^2$ is an ethyl group, $R^3$ represents a methyl group or a linear or branched alkyl group with a carbon number of 3 to 5. Examples of the linear or branched alkyl group with a carbon number of 2 to 5 include an ethyl group, a propyl group, an isopropyl group, a butyl group, an isobutyl group, a sec-butyl group, a tert-butyl group, a pentyl group, an amyl group, and an isoamyl group. Examples of the linear or branched alkyl group with a carbon number of 3 to 5 include a propyl group, an isopropyl group, a butyl group, an isobutyl group, a sec-butyl group, a tert-butyl group, a pentyl group, an amyl group, and an isoamyl group. Further, the copper compound represented by General Formula (I) can have a photoactive moiety. In such a case, the compound can be an R modification or an S modification, or a mixture including the R modification and S modification at a random ratio. In particular, where the copper compound is a mixture of the R modification and S modification, from the standpoint of production cost, it is preferred that the racemic modification be used.

The copper compound having the above-described structure has a low melting point, can be conveyed in a liquid state, has a high vapor pressure, and can be easily vaporized.

Further, as represented by General Formula (II) below, in the copper compound, a ring structure may be formed by coordination of the nitrogen atom in the ligand to the copper atom. In the present specification, the copper compound represented by General Formula (I) is a concept inclusive of the copper compound represented by General Formula (II).

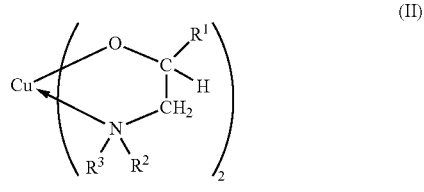

(II)

In General Formula (II), $R^1$ to $R^3$ independently represent a linear or branched alkyl group with a carbon number of 1 to 5; provided that $R^1$ and $R^2$ are a methyl group, $R^3$ represents a linear or branched alkyl group with a carbon number of 2 to 5; and provided that $R^1$ is a methyl group and $R^2$ is an ethyl group, $R^3$ represents a methyl group or a linear or branched alkyl group with a carbon number of 3 to 5.

When a vapor thin-film formation method is used by which a film is formed by vaporizing a copper compound, it is desirable that the copper compound be in a liquid state at normal temperature and under normal pressure, or have a low melting point when in a solid state, and also have a high vapor pressure. The copper compound having the structure such as described hereinabove generally has such properties. In particular, the copper compound in which $R^2$ is a methyl group, $R^3$ is an ethyl group, and R1 is a linear or branched alkyl group with a carbon number of 1 to 5 in General Formula (I) has an especially low melting point. Further, the carbon compound in which R1 is a methyl group or an ethyl group, $R^2$ is a methyl group, and $R^3$ is an ethyl group in General Formula (I) has a higher vapor pressure and a particularly low melting point. Furthermore, the copper compound in which $R^1$ is an ethyl group and $R^2$ and $R^3$ are each a methyl group in General Formula (I) has a higher vapor pressure.

Meanwhile, where a film is formed by the MOD method, it is desirable that a copper compound excels in solubility and the like in the solvent used. The copper compound having the structure such as described hereinabove generally has such a property. A copper compound particularly suitable for the MOD method can be easily obtained by selecting, as appropriate, $R^1$ to $R^3$ in General Formula (I) according to the type of the solvent to be used, thin film formation reaction, and the like.

Specific examples of the copper compound of the present invention are compounds No. 1 to No. 28 below. However, the copper compound of the present invention is not limited to the compounds listed below. In the chemical formulas below, "Me" represents a methyl group, "Et" represents an ethyl group, "iPr" represents an isopropyl group, "iBu" represents an isobutyl group, "sBu" represents a sec-butyl group, and "tBu" represents a tert-butyl.

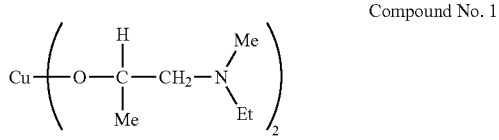

Compound No. 1

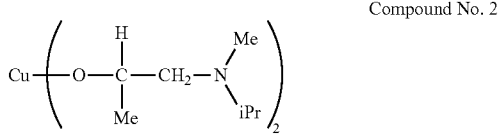

Compound No. 2

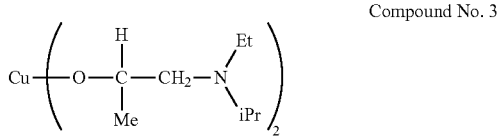

Compound No. 3

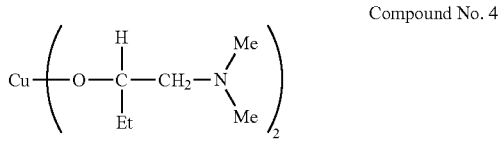

Compound No. 4

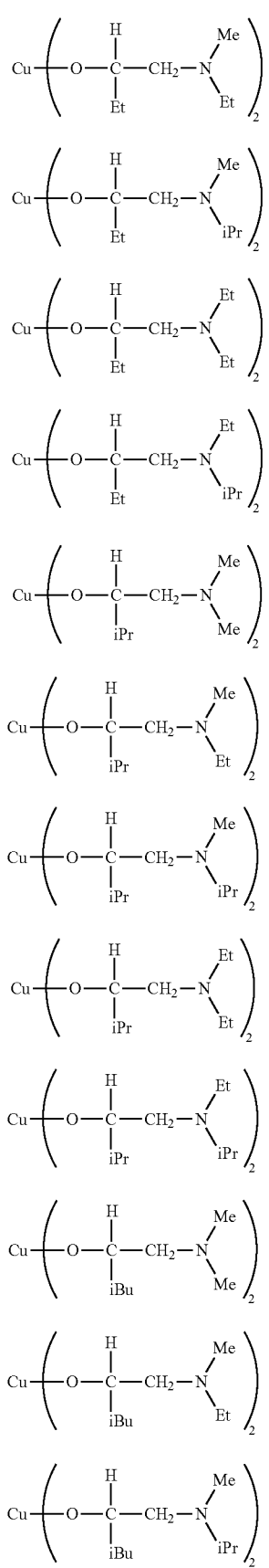
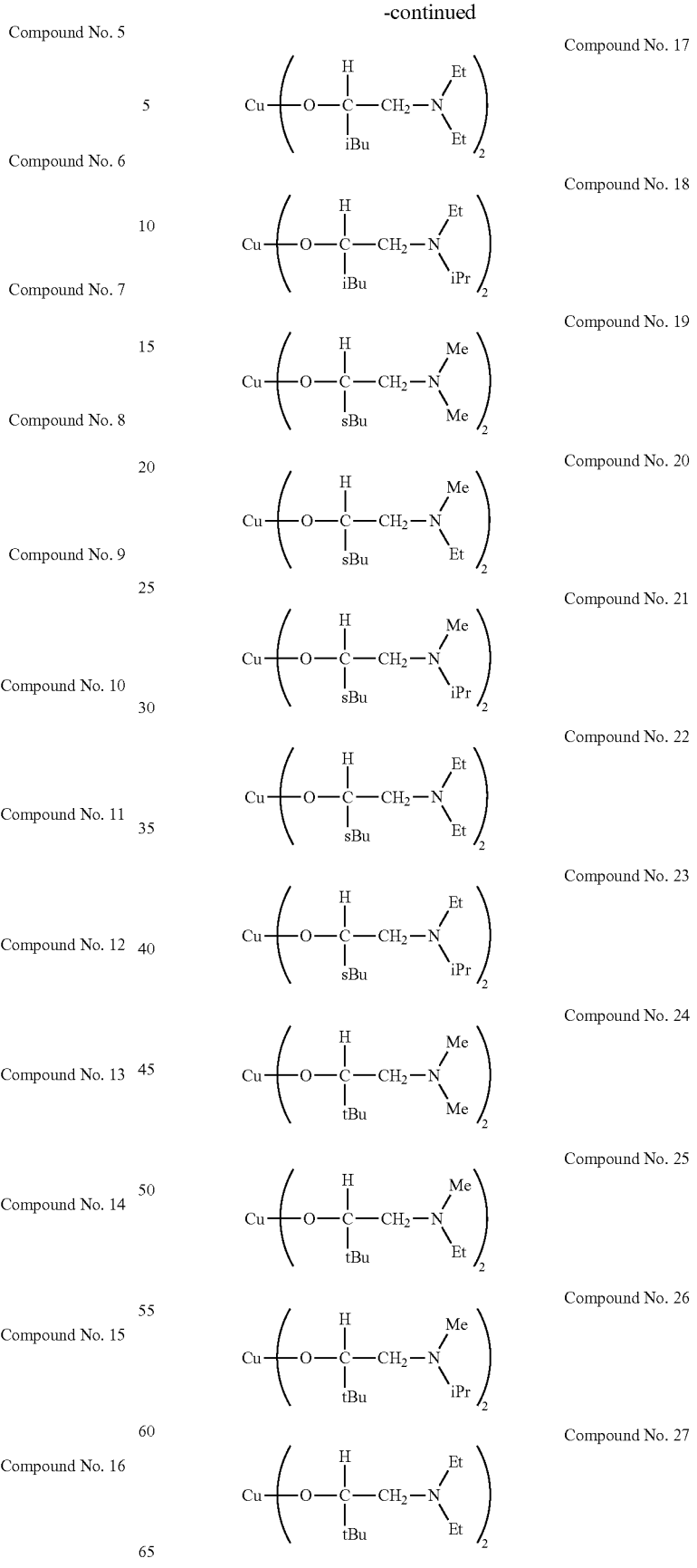

-continued

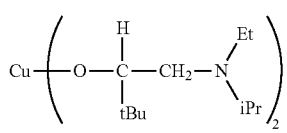

Compound No. 28

A method for manufacturing the copper compound of the present invention is not particularly limited, and the compound can be manufactured by making use of well-known reactions. More specifically, the copper compound of the present invention can be manufactured by using a well-known alkoxide compound synthesis method using an aminoalcohol. Examples of suitable methods include a method of conducting a reaction of an inorganic copper salt such as halide and nitrate, or a hydrate thereof with an aminoalcohol compound, which provides the predetermined ligand, in the presence of a base such as sodium, sodium hydride, sodium amide, sodium hydroxide, sodium methylate, ammonia, and amine; a method of conducting a reaction of an inorganic copper salt such as halide and nitrate, or a hydrate thereof with an alkali metal alkoxide, such as sodium alkoxide, lithium alkoxide, and potassium alkoxide which provides the predetermined ligand; a method of conducting an exchange reaction of a copper alkoxide compound of a low-molecular alcohol, such as methoxide, ethoxide, isopropoxide, and butoxide, with an alcohol compound which provides the predetermined ligand; and a method of reacting an inorganic copper salt such as halide and nitrate with a derivative which provides a reactive intermediate, thereby obtaining the reactive intermediate, and then reacting the reactive intermediate with the alcohol compound which provides the predetermined ligand. Examples of the reactive intermediate include amido compounds of copper such as bis(dialkylamino)copper and bis (bis(trimethylsilyl)amino)copper.

The copper compound having the above-described features has a low melting point, can be conveyed in a liquid state, has a high vapor pressure, and can be easily vaporized. Therefore, this compound is suitable as a starting material for forming a thin film that feeds copper to a thin film formed by a variety of methods for manufacturing thin films, in particular, the vapor thin-film formation method.

The starting material for forming a thin film of the present invention includes the copper compound of the present invention, which is represented by General Formula (I), as a precursor. The composition of the starting material for forming a thin film of the present invention differs depending on the type of the thin film which is to be produced, and where a thin film is formed that includes only copper as a metal, the starting material for forming a thin film of the present invention includes only the copper compound represented by General Formula (I) and does not include metal compounds or semimetal compounds other than the copper compound. Meanwhile, where a thin film is formed that includes, as the metal, copper and a metal and/or a semimetal other than copper, the starting material for forming a thin film of the present invention includes a compound including a metal other than copper and/or a compound including a semimetal (referred to hereinbelow as "other precursor") in addition to the copper compound represented by General Formula (I).

When the starting material for forming a thin film of the present invention includes the other precursor, the amount of the other precursor is preferably 0.01 mol to 10 mol, more preferably 0.1 mol to 5 mol per 1 mol of the copper compound represented by General Formula (I).

Further, as will be described hereinbelow, the starting material for forming a thin film of the present invention can also include an organic solvent and/or a nucleophilic reagent.

Since physical properties of the copper compound of the present invention, which serves as the precursor, are advantageous for methods for vapor-phase forming a thin film, in particular, the CVD method and ALD method, as has been explained hereinabove, the starting material for forming a thin film of the present invention is particularly useful as a starting material for such formation methods (referred to hereinbelow as "starting material for vapor-phase forming a thin film").

Where the starting material for forming a thin film of the present invention is a starting material for vapor-phase forming a thin film, the form thereof can be selected, as appropriate, according, e.g., to the conveying and feed method in the vapor thin-film formation method which is to be used.

The conveying and feed method can be a gas conveying method in which a starting material for vapor-phase forming a thin film is vaporized by heating and/or depressurizing the interior of a starting material container, and the obtained vapor is introduced, optionally together with a carrier gas such as argon, nitrogen, and helium, into a film deposition chamber in which a substrate is disposed; or a liquid conveying method in which a starting material for vapor-phase forming a thin film is conveyed in a liquid state into a vaporization chamber and vaporized by heating and/or depressurizing in the vaporization chamber, and the vapor is introduced into a film deposition chamber in which a substrate is disposed.

When the gas conveying method is used, the starting material for vapor-phase forming a thin film is used that can be vaporized by heating and/or depressurization. Meanwhile, when the liquid conveying method is used, the starting material for vapor-phase forming a thin film is used that is in a liquid state at a normal temperature and under a normal pressure. Therefore, when the liquid conveying method is used, where the copper compound is in a liquid form at a normal temperature and under a normal pressure, the copper compound in a liquid form can be used as the starting material for vapor-phase forming a thin film, but where the copper compound is in a solid form at a normal temperature and under a normal pressure, the copper compound dissolved in an organic solvent is used as the starting material for vapor-phase forming a thin film.

Further, the vapor thin-film formation method which uses a multicomponent system can be implemented by a method of vaporizing and feeding each component independently (referred to hereinbelow as "single source method") and a method of vaporizing and feeding a mixed starting material obtained by mixing the components in advance at the desired composition ratio (referred to hereinbelow as "cocktail source method"). When the cocktail source method is used, a mixture of the copper compound of the present invention and the other precursor, or a mixed solution obtained by dissolving the mixture in an organic solvent can be used as the starting material for vapor-phase forming a thin film.

The organic solvent to be used with the starting material for vapor-phase forming a thin film of the present invention is not particularly limited, and typical organic solvents known in the pertinent technical field can be used. Examples of the organic solvents include acetic acid esters such as ethyl acetate, butyl acetate, and methoxyethyl acetate; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; hydrocarbons including a cyano group such as 1-cyanopropane, 1-cyanobutane, 1-cyanohexane, cyanocyclohexane, cycanobenzene, 1,3-dicyanopropane, 1,4-dicyanobutane, 1,6-dicyanohexane, 1,4-dicyanocyclohexane, and 1,4-dicyanobenzene; pyridine and lutidine. Such organic solvents are used individually or as mixed solvents of two or more thereof according to the relationship between the solute solubility, usage temperature, boiling point, and flash point.

When the starting material for vapor-phase forming a thin film of the present invention uses an organic solvent, the total amount of the copper compound of the present invention and the other precursor in the organic solvent is preferably 0.01 mol/L to 2.0 mol/L, and more preferably 0.05 mol/L to 1.0 mol/L.

The other precursor used in the starting material for vapor-phase forming a thin film of the present invention is not particularly limited and typical precursors known in the pertinent technical field can be used. Examples of the other precursor include compounds of silicon or a metal (excluding copper) and one or two or more organic coordination compounds such as alcohol compounds, glycol compound, β-diketone compound, cyclopentadiene compound, organic amine compound, and ketimine compound. The metal species are not particularly limited, and examples thereof include magnesium, calcium, strontium, barium, radium, scandium, yttrium, titanium, zirconium, hafnium, vanadium, niobium, tantalum, chromium, molybdenum, tungsten, manganese, iron, osmium, ruthenium, rhodium, iridium, nickel, palladium, platinum, silver, gold, zinc, cobalt, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium.

The alcohol compound providing the organic ligand of the other precursor is not particularly limited and examples thereof include alkyl alcohols such as methanol, ethanol, propanol, isopropyl alcohol, butanol, sec-butyl alcohol, isobutyl alcohol, tert-butyl alcohol, pentyl alcohol, isopentyl alcohol, and tert-pentyl alcohol; ether alcohols such as 2-methoxyethanol, 2-ethoxyethanol, 2-butoxyethanol, 2-(2-methoxyethoxy)ethanol, 2-methoxy-1-methyl ethanol, 2-methoxy-1,1-dimethyl ethanol, 2-ethoxy-1,1-dimethyl ethanol, 2-isopropoxy-1,1-dimethyl ethanol, 2-butoxy-1,1-dimethyl ethanol, 2-(2-methoxyethoxy)-1,1-dimethyl ethanol, 2-propoxy-1,1-diethyl ethanol, 2-s-butoxy-1,1-diethyl ethanol, and 3-methoxy-1,1-dimethyl-propanol; and aminoalcohols such as 1-dimethylamino-2-propanol, 1-ethylmethylamino-2-propanol, 1-diethylamino-2-propanol, 1-dimethylamino-2-methyl-2-propanol, 1-ethyl methylamino-2-methyl-2-propanol, 1-diethylamino-2-methyl-2-propanol, 1-dimethylamino-2-butanol, 1-ethylmethylamino-2-butanol, 1-diethylamino-2-butanol, 1-dimethylamino-2-methyl-2-butanol, 1-ethylmethylamino-2-methyl-2-butanol, and 1-diethylamino-2-methyl-2-butanol.

The glycol compound providing the organic ligand of the other precursor is not particularly limited and examples thereof include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

The β-diketone compound providing the organic ligand of the other precursor is not particularly limited, and examples thereof include alkyl-substituted β-diketones such as acetylacetone, hexane-2,4-dione, 5-methylhexane-2,4-dione, heptane-2,4-dione, 2-methylheptane-3,5-dione, and 2,6-dimethylheptane-3,5-dione; fluorine-substituted alkyl β-diketones such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; ether-substituted β-diketones such as 1,1,5,5-tetramethyl-1-methoxyhexane-2,4-dione, 2,2,6,6 tetramethyl-1-methoxyheptane-3,5-dione, and 2,2,6,6-tetramethyl-1-(2-methoxyethoxy)heptane-3,5-dione.

The cyclopentadiene compound providing the organic ligand of the other precursor is not particularly limited, and examples thereof include cyclopentadiene, methyl cyclopentadiene, ethyl cyclopentadiene, propyl cyclopentadiene, isopropyl cyclopentadiene, butyl cyclopentadiene, sec-butyl cyclopentadiene, isobutyl cyclopentadiene, tert-butyl cyclopentadiene, dimethyl cyclopentadiene, and tetramethyl cyclopentadiene.

The organic amine compound providing the organic ligand of the other precursor is not particularly limited, and examples thereof include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, isopropylmethylamine, ethylenediamine, and N,N-dimethylethylenediamine.

The ketimine compound providing the organic ligand of the other precursor is not particularly limited, and examples thereof include reaction products of the aforementioned β-diketone compound and organic amine compound. More specifically, a ketimine compound, etc. obtained by reacting acetylacetone and N,N-dimethylethylenediamine in the presence of hydrogen chloride can be used.

In the case of a single source method, it is preferred that the other precursor be similar in thermal and/or oxidative decomposition behavior to the copper compound of the present invention. In the case of a cocktail source method, it is preferred that the other precursor be similar in thermal and/or oxidative decomposition behavior to the copper compound of the present invention and also demonstrate no transformations induced by chemical reactions at the time of mixing.

Among the other precursors, the precursors having titanium, zirconium, or hafnium as the metal species are represented by General Formulas (III-1) to (III-5) below.

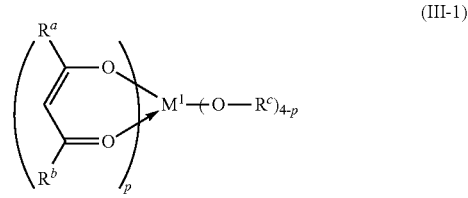

(III-1)

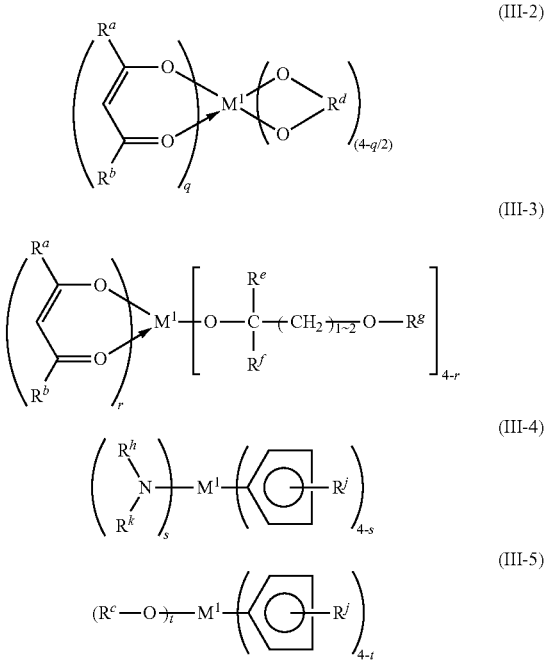

In General Formulas (III-1) to (III-5), $M^1$ represents titanium, zirconium, or hafnium; $R^a$ and $R^b$ independently represent an alkyl group with a carbon number of 1 to 20 which may be substituted with a halogen atom and may contain an oxygen atom in a chain; $R^c$ represents an alkyl group with a carbon number of 1 to 8; $R^d$ represents an optionally branched alkylene group with a carbon number of 2 to 18; $R^e$ and $R^f$ independently represent a hydrogen atom or an alkyl group with a carbon number of 1 to 3; $R^g$, $R^h$, $R^k$, and $R^j$ independently represent a hydrogen atom or an alkyl group with a carbon number of 1 to 4; p represents an integer of 0 to 4; q represents 0 or 2; r represents an integer of 0 to 3; s represents an integer of 0 to 4; and t represents an integer of 1 to 4.

Examples of the alkyl group with a carbon number of 1 to 20 which may be substituted with a halogen atom and may contain an oxygen atom in a chain, this group being represented by $R^a$ and $R^b$ in General Formulas (III-1) to (III-5), include methyl, ethyl, propyl, isopropyl, butyl, sec-butyl, tert-butyl, isobutyl, amyl, isoamyl, sec-amyl, tert-amyl, hexyl, cyclohexyl, 1-methylcyclohexyl, heptyl, 3-heptyl, isoheptyl, tert-heptyl, n-octyl, isooctyl, tert-octyl, 2-ethylhexyl, trifluoromethyl, perfluorohexyl, 2-methoxyethyl, 2-ethoxyethyl, 2-butoxyethyl, 2-(2-methoxyethoxy)ethyl, 1-methoxy-1,1-dimethylmethyl, 2-methoxy-1,1-dimethylethyl, 2-ethoxy-1,1-dimethylethyl, 2-isopropoxy-1,1-dimethylethyl, 2-butoxy-1,1-dimethylethyl, and 2-(2-methoxyethoxy)-1,1-dimethylethyl.

Examples of the alkyl group with a carbon number of 1 to 8 which is represented by $R^c$ include methyl, ethyl, propyl, isopropyl, butyl, sec-butyl, tert-butyl, isobutyl, amyl, isoamyl, sec-amyl, tert-amyl, hexyl, 1-ethylpentyl, cyclohexyl, 1-methylcyclohexyl, heptyl, isoheptyl, tert-heptyl, n-octyl, isooctyl, tert-octyl, and 2-ethylhexyl.

Further, the optionally branched alkylene group with a carbon number of 2 to 18 which is represented by $R^d$ is a group derived from a glycol. Examples of the glycol include 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol.

Examples of the alkyl group with a carbon number of 1 to 3 which is represented by $R^e$ and $R^f$ include methyl, ethyl, propyl, and 2-propyl. Examples of the alkyl group with a carbon number of 1 to 4 which is represented by Rg, Rh, Rj, and Rk include methyl, ethyl propyl, isopropyl, butyl, sec-butyl, tert-butyl, and isobutyl.

Specific examples of precursors including titanium as the metal species include tetrakis(alkoxy)titanium such as tetrakis(ethoxy)titanium, tetrakis(2-propoxy)titanium, tetrakis(butoxy)titanium, tetrakis(sec-butoxy)titanium, tetrakis(isobutoxy)titanium, tetrakis(tert-butoxy)titanium, tetrakis(tert-amyl)titanium, and tetrakis(1-methoxy-2-methyl-2-propoxy)titanium; tetrakis-β-diketonatotitanium such as tetrakis(pentane-2,4-dionato)titanium, (2,6-dimethylheptane-3,5-dionato)titanium, and tetrakis(2,2,6,6-tetramethylheptane-3,5-dionato)titanium; bis(alkoxy)bis(β-diketonato)titanium such as bis(methoxy)bis(pentane-2,4-dionato)titanium, bis(ethoxy)bis(pentane-2,4-dionato)titanium, bis(tert-butoxy)bis(pentane-2,4-dionato)titanium, bis(methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato)titanium, bis(tert-amyloxy)bis(2,6-dimethylheptane-3,5-dionato)titanium, bis(methoxy)bis(2,2,6,6-tetramethylheptane-3,5-dionato)titanium, bis(ethoxy)bis(2,2,6,6-tetramethylheptane-3,5-dionato)titanium, bis(2-propoxy)bis(2,6,6,6-tetramethylheptane-3,5-dionato)titanium, bis(tert-butoxy)bis(2,2,6,6-tetramethylheptane-3,5-dionato)titanium, and bis(tert-amyloxy)bis(2,2,6,6-tetramethylheptane-3,5-dionato)titanium; glycoxybis(β-diketonato)titanium such as (2-methylpentanedioxy)bis(2,2,6,6-tetramethylheptane-3,5-dionato)titanium and (2-methylpentanedioxy)bis(2,6-dimethylheptane-3,5-dionato)titanium; (cyclopentadienyl)tris(dialkylamino)titanium such as (methylcyclopentadienyl)tris(dimethylamino)titanium, (ethylcyclopentadienyl)tris(dimethylamino)titanium, (cyclopentadienyl)tris(dimethylamino)titanium, (methylcyclopentadienyl)tris(ethylmethylamino)titanium, (ethylcyclopentadienyl)tris(ethylmethylamino)titanium, (cyclopentadienyl)tris(ethylmethylamino)titanium, (methylcyclopentadienyl)tris(diethylamino)titanium, (ethylcyclopentadienyl)tris(diethylamino)titanium, and (cyclopentadienyl)tris(diethylamino)titanium; and (cyclopentadienyl)tris(alkoxy)titanium such as (cyclopentadienyl)tris(methoxy)titanium, (methylcyclopentadienyl)tris(methoxy)titanium, (ethylcyclopentadienyl)tris(methoxy)titanium, (propylcyclopentadienyl)tris(methoxy)titanium, (isopropylcyclopentadienyl)tris(methoxy)titanium, (butylcyclopentadienyl)tris(methoxy)titanium, (isobutylcyclopentadienyl)tris(methoxy)titanium, and tert-butylcyclopentadienyl)tris(methoxy)titanium. Specific examples of precursors including zirconium or hafnium as the metal species are compounds presented as examples of titanium-containing precursors in which titanium is substituted with zirconium or hafnium.

Examples of precursors that include rare earth metals as the metal species are compounds represented by General Formulas (IV-1) to (IV-3).

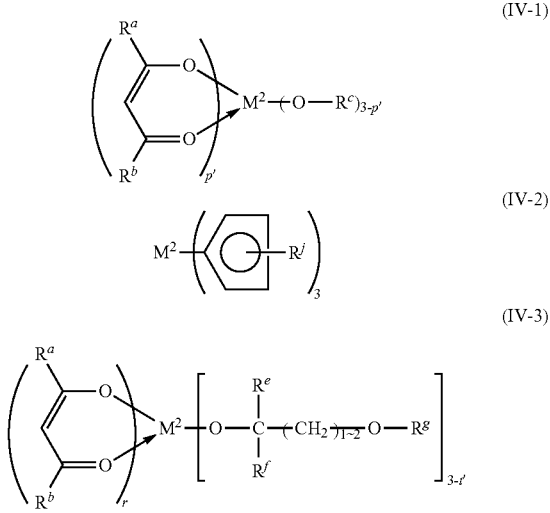

In General Formulas (IV-1) to (IV-3), $M^2$ represents a rare earth atom; $R^a$ and $R^b$ independently represent an alkyl group with a carbon number of 1 to 20 which may be substituted with a halogen atom and may contain an oxygen atom in a chain; $R^c$ represents an alkyl group with a carbon number of 1 to 8; $R^e$ and $R^f$ independently represent a hydrogen atom or an alkyl group with a carbon number of 1 to 3; $R^g$ and $R^j$ independently represent an alkyl group with a carbon number of 1 to 4; p' represents an integer of 0 to 3; and r' represents an integer of 0 to 2.

Examples of rare earth atoms represented by $M^2$ in General Formulas (IV-1) to (IV-3) include scandium, yttrium, lanthanum, cerium, praseodymium, promethium, samarium, europium, gadolinium, terbium, dysprosium, holmium, erbium, thulium, ytterbium, and lutetium. Examples of groups represented by $R^a$, $R^b$, $R^c$, $R^e$, $R^f$, $R^g$, and $R^j$ include groups presented by way of examples with respect to the precursors including titanium, and the like, as the metal species.

If necessary, the starting material for forming a thin film of the present invention may include a nucleophilic reagent to stabilize the copper compound of the present invention and the other precursor. The nucleophilic reagent is not particularly limited, and examples thereof include ethylene glycol ethers such as glyme, diglyme, triglyme, and tetraglyme; crown ethers such as 18-crown-6, dicyclohexyl-18-crown-6, 24-crown-8, dicyclohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters such as methyl acetoacetate, ethyl acetoacetate, and 2-methoxyethyl acetoacetate; and β-diketones such as acetylacetone, 2,4-hexanedione, 2,4-heptanedione, and 3,5-heptanedione.

These nucleophilic reagents are used in an amount usually within a range of 0.1 mol to 10 mol, and preferably within a range of 1 mol to 4 mol per 1 mol of the precursor.

In the starting material for forming a thin film of the present invention, the amount of metal element impurities, halogen impurities such as chlorine-containing impurities, and organic impurities, which are different from the above-mentioned components, needs to be minimized. The amount of the metal element impurities is preferably 100 ppb or less, and more preferably 10 ppb or less for each element, and the total amount of the impurities is preferably 1 ppm or less, and more preferably 100 ppb or less. In particular, when the starting material for forming a thin film of the present invention is used to produce a gate insulating layer, a gate film, a barrier layer of an LSI, and the like, it is necessary to reduce the amount of alkali metal elements, alkaline earth metal elements, and analogous elements which affect the electric properties of the resulting thin film. The amount of the halogen impurities is preferably 100 ppm or less, more preferably 10 ppm or less, and even more preferably 1 ppm or less. The total amount of organic impurities is preferably 500 ppm or less, more preferably 50 ppm or less, and most preferably 10 ppm or less.

Further, since moisture contained in the starting material for forming a thin film causes particle generation in the starting material for forming a thin film or particle generation during thin film formation, it is better to remove moisture as much as possible, prior to use, from the precursor, organic solvent, and nucleophilic reagent in order to reduce the amount of moisture therein. The amount of moisture in each of the precursor, organic solvent, and nucleophilic reagent is preferably 10 ppm or less, and more preferably 1 ppm or less.

Further, in order to reduce or prevent the particle contamination of the thin film to be formed, it is preferred that the starting material for forming a thin film of the present invention include as few particles as possible. More specifically, in particle measurements with a particle detector of a light scattering type in a liquid phase, the number of particles larger than 0.3 μm is preferably 100 or less in 1 mL of the liquid phase, more preferably the number of particles larger than 0.2 μm is 1000 or less in 1 mL of the liquid phase, and even more preferably the number of particles larger than 0.2 μm is 100 or less in 1 mL of the liquid phase.

A method for manufacturing a thin film of the present invention is performed using the starting material for forming a thin film of the present invention. The method for manufacturing a thin film of the present invention which is performed using the starting material for forming a thin film of the present invention is not particularly limited, and a MOD method such as a coating and thermal decomposition method and a sol-gel method, or a vapor thin-film formation method such as an ALD method and a CVD method can be used. Among them, the vapor thin-film formation method is preferred since this method has a large number of merits, such as excellent composition controllability and step coverage ability, suitability for mass production, and capability to enable hybrid accumulation.

The method for manufacturing a thin film of the present invention that is performed using the vapor thin-film formation method includes a step of vaporizing the starting material for forming a thin film of the present invention to obtain a vapor including a copper compound, and a step of contacting the vapor with a substrate to decompose and/or chemically react the copper compound and then to form a thin film on the substrate. The thin film is generally formed in a film deposition chamber in which the substrate is disposed. The thin film may be formed by feeding the vapor including the copper compound optionally together with a reactive gas into the film deposition chamber. The starting material for forming a thin film may be fed into the film deposition chamber, in which the substrate is disposed, by using the above-described gas conveying method, liquid conveying method, single source method, and cocktail source method.

Examples of the vapor thin-film formation method include a thermal CVD method in which a source material gas (vaporized source material for forming a thin film) or a source material gas and a reactive gas are reacted by using only heat in order to form a thin film; a plasma CVD method in which heat and plasma are used; a photo-excited CVD method in which heat and light are used; a photo- and plasma-excited CVD method in which heat, light and plasma are used; and an ALD method in which the CVD deposition reaction is separated into elementary steps and deposition is performed step by step at a molecular level.

The optionally used reactive gas is not particularly limited, and examples thereof include oxidative gases such as oxygen, ozone, nitrogen dioxide, nitrogen monoxide, water vapor, hydrogen peroxide, formic acid, acetic acid, and acetic anhydride, and reductive gases such as hydrogen. Further, where a thin film including a nitride is formed, organic amine compounds such as monoalkylamines, dialkylamines, trialkylamines, and alkylenediamines, and also hydrazine, ammonia, and the like may be used as the reactive gases. These reactive gases can be used individually or in combinations of two or more thereof.

The film formation conditions inside the film deposition chamber are not particularly limited and may be set, as appropriate, according to the type of the device and starting materials which are to be used. The device for producing a thin film is not particularly limited, and devices for vapor-phase forming a thin film, such as a chemical vapor deposition device, which are well known in the pertinent technical field can be used. Examples of the devices for forming a thin film include a device for vapor-phase forming a thin film in which the starting material for forming a thin film can be fed by bubbling, a device for vapor-phase forming a thin film which has a vaporization chamber for vaporizing the starting material for forming a thin film, and a device for vapor-phase forming a thin film in which plasma treatment can be performed. These devices are not limited to single-substrate devices and can be devices using a batch furnace and capable of simultaneously processing a large number of substrates.

Examples of film formation conditions typically include a reaction temperature (substrate temperature), a reaction pressure, and a deposition rate. The reaction temperature is preferably 100° C. or higher, at which, for instance, the copper compound of the present invention is sufficiently reactive, and more preferably 100° C. to 400° C.

The reaction pressure is preferably from atmospheric pressure to 10 Pa for thermal CVD and photo-excited CVD, and preferably from 2000 Pa to 10 Pa when plasma is used.

The deposition rate can be controlled by the starting material feed conditions (vaporization temperature and vaporization pressure), reaction temperature, and reaction pressure.

Where the deposition rate is too high, properties of the resulting thin film can be degraded, and where the deposition rate is too low, productivity can be a problem. For these reasons, the deposition rate is preferably 0.01 nm/min to 5000 nm/min and more preferably 0.1 nm/min to 1000 nm/min. Further, in the ALD method, the control is performed by the number of cycles so as to obtain the desired film thickness.

For example, when a copper thin film is formed by using the ALD method, a precursor thin film is formed using the starting material for forming a thin film of the present invention. More specifically, the starting material for forming a thin film of the present invention is vaporized to obtain a vapor including a copper compound, and the vapor is then brought into contact with a substrate, thereby causing decomposition and/or chemical reaction of the copper compound and forming a precursor thin film on the substrate (precursor thin film formation step). At this time, heat may be applied by heating the substrate or heating the film deposition chamber. The substrate temperature is preferably from room temperature to 500° C., more preferably from 150° C. to 350° C. The pressure in the film deposition chamber is preferably 1 Pa to 10,000 Pa, and more preferably 10 Pa to 1000 Pa. The precursor thin film which is formed is a thin film generated by decomposition and/or reaction of part of the copper compound and has a composition different from the target copper thin film.

The unreacted starting material gas and byproduct gas are then evacuated from the film deposition chamber (evacuation step). The unreacted starting material gas and byproduct gas are ideally completely evacuated from the film deposition chamber, but such complete evacuation is not always necessary. Examples of the evacuation method include a method of purging the interior of the film deposition chamber with an inactive gas such as nitrogen, helium, and argon, a method of evacuating by depressurizing the interior of the film deposition chamber, and a method in which the aforementioned methods are combined. The degree of depressurization when the depressurization method is used is preferably 0.01 Pa to 300 Pa, and more preferably 0.01 Pa to 100 Pa.

The reactive gas is then fed into the film deposition chamber, and a copper thin film is formed from the precursor thin film under the action of the reactive gas or the action of the reactive gas and heat (copper thin film formation step). The heating temperature in this case is preferably from room temperature to 500° C., and more preferably from 150° C. to 350° C. The copper compound of the present invention has good reactivity with reactive gas represented by hydrogen, oxygen, and ozone, and a copper thin film or copper oxide thin film can be formed with good efficiency.

When the ALD method is used in the above-described manner for manufacturing a copper thin film, the series of steps including the precursor thin film formation step, evacuation step, and copper thin film formation step may be taken as one cycle, and such cycles may be repeated a plurality of times till a copper thin film of a necessary thickness is obtained. In this case, after one cycle is completed, it is preferred that the unreacted starting material gas, reactive gas, and byproduct gas be evacuated from the film deposition chamber in the same manner as in the evacuation step, and the next cycle be thereafter performed.

In a method for forming a cobalt oxide thin film by using the ALD method, energy such as plasma, light, and voltage may be applied. The timing for applying the energy is not particularly limited. For example, the energy may be applied between or during the aforementioned steps.

Further, in the method for manufacturing a thin film of the present invention, annealing may be performed under an inactive gas atmosphere, an oxidizing atmosphere, or a reducing atmosphere after the thin film has been formed to obtain better electric properties. Silicidation may be also performed for the same purpose. A reflow step may be employed when bump embedding is needed. In this case, the temperature is usually 200° C. to 1000° C. and preferably 250° C. to 500° C.

The thin film manufactured by the method for manufacturing a thin film of the present invention that used the starting material for forming a thin film of the present invention can be manufactured as a thin film of a desired type, such as a metal, oxide ceramic, nitride ceramic, and glass by selecting, as appropriate, other precursors, reactive gases, manufacturing conditions, and the like. More specifically, thin films of copper, copper-based oxides, copper-based nitrides, and the like can be manufactured. Such thin films can be used for wiring, electrodes, etc. for LSI.

EXAMPLES

The present invention will be explained hereinbelow in greater detail with reference to examples and comparative examples. However, the present invention is not limited by the below-described examples, and the like.

Example 1: Compound No. 1

A total of 15.0 g (119 mmol) of copper (II) methoxide and 140 g of toluene were charged into a 1000 mL three-neck flask and stirred at room temperature. A total of 29.0 g (238 mmol) of 1-(ethyl(methyl)amino)-2-propanol was gradually added dropwise thereto. Upon completion of the dropwise addition, the liquid mixture was reacted for 20 hrs at room temperature. Methanol as a byproduct was distilled off under atmospheric pressure and at a bath temperature of 80° C. The toluene solvent was then distilled off under a reduced pressure and a bath temperature of 100° C. The remaining viscous liquid was subjected to distillation purification at a bath temperature of 105° C., a pressure of 60 Pa, and a column top temperature of 85° C. to 88° C. to obtain a target product (Compound No. 1) in the form of a violet viscous liquid. The yield amount was 20.0 g and the yield ratio was 56.8%.

Elemental analysis (metal analysis: ICP-AES) was performed with respect to the resulting target product (Compound No. 1). The results are presented below.

Copper: 21.8 Mass % (Theoretical Value 21.5 Mass %)
C: 47.9 mass %, H: 9.66 mass %, N: 9.33 mass % (theoretical values; C: 48.7 mass %, H: 9.54 mass %, N: 9.47 mass %)

Example 2: Compound No. 4

A total of 15.0 g (119 mmol) of copper (II) methoxide and 140 g of toluene were charged into a 1000 mL three-neck flask and stirred at room temperature. A total of 29.0 g (238 mmol) of 1-dimethylamino-2-butanol was gradually added dropwise thereto. Upon completion of the dropwise addition, the liquid mixture was reacted for 20 hrs at room temperature. Methanol as a byproduct was distilled off under atmospheric pressure and at a bath temperature of 80° C. The toluene solvent was then distilled off under a reduced pressure and a bath temperature of 100° C. The residue was subjected to distillation purification at a bath temperature of 105° C., a pressure of 60 Pa, and a column top temperature of 88° C. to 90° C., and then cooled to room temperature to obtain a target product (Compound No. 4) in the form of a violet solid matter. The melting point was 80° C., the yield amount was 18.0 g, and the yield ratio was 51.1%.

Elemental analysis (metal analysis: ICP-AES) was performed with respect to the resulting target product (Compound No. 4). The results are presented below.

Copper: 20.7 Mass % (Theoretical Value 21.5 Mass %)
C: 48.1 mass %, H: 9.60 mass %, N: 9.10 mass % (theoretical values; C: 48.7 mass %, H: 9.54 mass %, N: 9.47 mass %)

Example 3: Compound No. 5

A total of 15.0 g (119 mmol) of copper (II) methoxide and 140 g of toluene were charged into a 1000 mL three-neck flask and stirred at room temperature. A total of 31.2 g (238 mmol) of 1-(ethyl(methyl)amino)-2-butanol was gradually added dropwise thereto. Upon completion of the dropwise addition, the liquid mixture was reacted for 20 hrs at room temperature. Methanol as a byproduct was distilled off under atmospheric pressure and at a bath temperature of 80° C. The toluene solvent was then distilled off under a reduced pressure and a bath temperature of 100° C. The residue was subjected to distillation purification at a bath temperature of 115° C., a pressure of 60 Pa, and a column top temperature of 90° C. to 95° C. to obtain a target product (Compound No. 5) in the form of a violet viscous liquid. The yield amount was 20.0 g and the yield ratio was 52.0%.

Elemental analysis (metal analysis: ICP-AES) was performed with respect to the resulting target product (Compound No. 5). The results are presented below.

Copper: 20.2 Mass % (Theoretical Value 19.6 Mass %)
51.3 mass %, H: 10.1 mass %, N: 8.80 mass % (theoretical values; C: 51.9 mass %, H: 9.96 mass %, N: 8.65 mass %)

Comparative Examples 1 to 3

Comparative Compounds No. 1, No. 2, and No. 3 were manufactured according to well-known methods as Comparative Examples 1, 2, and 3, respectively.

Comparative Compound No. 1

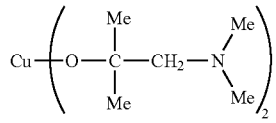

Comparative Compound No. 2

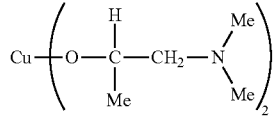

Comparative Compound No. 3

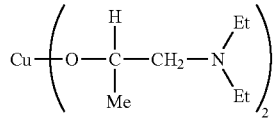

The state (whether solid or liquid), at normal temperature (30° C.), of the copper compounds obtained in the examples and comparative examples was visually observed, and for the compounds in a solid state, the melting point was measured using a micro-melting point measurement device.

The TG-DTA was also performed under the below-described measurement conditions with respect to the copper compounds obtained in the examples and comparative examples, and the temperature at the time of 50% weight reduction of the sample was measured.

(Measurement Conditions)
Pressure: 10 Torr
Ar flow rate: 50 mL/min
Rate of temperature rise: 10° C./min
Sample weight: about 10 mg
The evaluation results are shown in Table 1.

TABLE 1

| | Type of compound | State at normal temperature | Melting point (° C.) | Temperature at 50% weight reduction (° C.) |
|---|---|---|---|---|
| Example 1 | Compound No. 1 | Solid | 38 | 100 |
| Example 2 | Compound No. 4 | Solid | 80 | 100 |
| Example 3 | Compound No. 5 | Liquid | — | 110 |
| Comparative Example 1 | Comparative Compound No. 1 | Solid | *1 | 100 |
| Comparative Example 2 | Comparative Compound No. 2 | Solid | >100 | 120 |
| Comparative Example 3 | Comparative Compound No. 3 | Solid | *2 | 130 |

*1 Did not become a liquid, sublimated and became a gas.
*2 Since the temperature at 50% weight reduction was high and the vapor pressure increased, the measurement of melting point was omitted.

As indicated by the results presented in Table 1, the copper compounds of Examples 1 to 3 were liquid or solid matter with a low melting point. Since the starting material for forming a thin film which is a liquid or has a low melting point is easy to convey, the copper compounds of Examples 1 to 3 can be said to be starting materials for forming a thin film which make it possible to increase the productivity. Further, since the copper compounds of Examples 1 to 3 have a low temperature at the time of 50% weight reduction of the sample, these compounds can be said to be starting materials for forming a thin film which have a high vapor pressure.

By contrast, the copper compound of Comparative Example 1 has a very small difference between the melting point and boiling point and is difficult to convey in a liquid state. Therefore, this compound is apparently not suitable as a starting material for forming a thin film.

Further, the copper compounds of Comparative Examples 2 and 3 have a high temperature at the time of 50% weight reduction of the sample and also have a low vapor pressure. Therefore, these compounds are apparently not suitable as starting materials for forming a thin film.

Example 4: Manufacture of Copper Thin Film by ALD Method

Copper compounds of Examples 1 to 3 were used as starting materials for forming a thin film, and copper thin films were formed on silicon wafers by the plasma ALD method under the below-described conditions in the plasma ALD device depicted in FIG. 1.

<Conditions>
Temperature in starting material container: 60° C.
Pressure in starting material container: 100 Pa
Reaction temperature (substrate temperature): 60° C.
Reactive gas: hydrogen gas
Carrier gas: argon gas
<Steps>
The following steps (1) to (4) were taken as 1 cycle, and 300 cycles were performed.

(1) The vapor of the vaporized starting material for forming a thin film was fed into the film deposition chamber, and deposition was performed for 10 s under a pressure of 100 Pa in the film deposition chamber.

(2) The unreacted starting material for forming a thin film was removed by purging with argon for 5 s.

(3) The reactive gas and plasma were fed into the film deposition chamber and the reaction was conducted for 10 s under a pressure of 100 Pa in the film deposition chamber.

(4) The unreacted reactive gas and plasma were removed by purging with argon for 5 s.

Film thickness measurements by an X-ray reflectance method and confirmation of thin film structure and thin film composition by an X-ray photoelectron spectroscopy were performed with respect to the manufactured thin films. The results indicate that the film thickness was 7 nm to 10 nm, the film composition was copper (confirmed by a Cu2p peak in XPS analysis), and the amount of carbon was less than 0.1 atom % which is a lower detection limit. The film thickness obtained in 1 cycle was 0.02 nm to 0.03 nm.

As follows from these results, the present invention can provide a copper compound which has a low melting point, can be conveyed in a liquid state, has a high vapor pressure, and is easily vaporizable, and also a starting material for forming a thin film which uses such a copper compound.

Further, the present invention can also provide a method for manufacturing a thin film that is suitable for manufacturing a copper-containing thin film of good quality with good productivity.

The present international application claims priority from Japanese Patent Application No. 2014-100611 filed on May 14, 2014. The contents of the Japanese Patent Application are incorporated in the present international application.

The invention claimed is:

1. A copper compound of the following formulae:

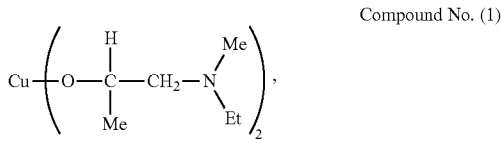

Compound No. (1)

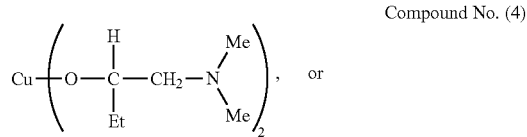

Compound No. (4)

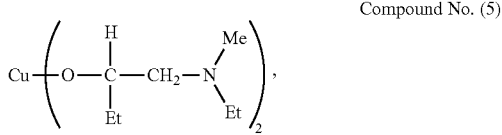

Compound No. (5)

wherein Me is a methyl group and Et is an ethyl group.

2. A starting material for forming a thin film, comprising the copper compound according to claim 1.

3. A method for manufacturing a thin film, comprising the steps of:
vaporizing the starting material for forming a thin film according to claim 2 to obtain a vapor including a copper compound; and
contacting the vapor with a substrate to decompose and/or chemically react the copper compound and then to form a thin film on the substrate.

* * * * *